US011352423B2

(12) United States Patent
Garidel et al.

(10) Patent No.: US 11,352,423 B2
(45) Date of Patent: Jun. 7, 2022

(54) ANTI-CD19 ANTIBODY FORMULATIONS

(71) Applicant: MorphoSys AG, Planegg (DE)

(72) Inventors: Patrick Garidel, Ingelheim am Rhein (DE); Andreas Langer, Ingelheim am Rhein (DE); Martin Hessling, Biberach an der Riß (DE); Daniel Weinfurtner, Planegg (DE); Bodo Brocks, Planegg (DE)

(73) Assignee: MORPHOSYS AG, Planegg (DE)

( * ) Notice: Subject to any disclaimer, the term of this patent is extended or adjusted under 35 U.S.C. 154(b) by 131 days.

(21) Appl. No.: 16/310,555

(22) PCT Filed: Jun. 27, 2017

(86) PCT No.: PCT/EP2017/065819
§ 371 (c)(1),
(2) Date: Dec. 17, 2018

(87) PCT Pub. No.: WO2018/002031
PCT Pub. Date: Jan. 4, 2018

(65) Prior Publication Data
US 2019/0322742 A1    Oct. 24, 2019

(30) Foreign Application Priority Data

Jun. 27, 2016 (EP) .................................. 16176322

(51) Int. Cl.
| | |
|---|---|
| C07K 16/28 | (2006.01) |
| A61K 47/54 | (2017.01) |
| A61K 9/19 | (2006.01) |
| A61K 47/36 | (2006.01) |
| A61K 31/715 | (2006.01) |

(52) U.S. Cl.
CPC ............ *C07K 16/2803* (2013.01); *A61K 9/19* (2013.01); *A61K 31/715* (2013.01); *A61K 47/36* (2013.01); *A61K 47/549* (2017.08)

(58) Field of Classification Search
None
See application file for complete search history.

(56) References Cited

U.S. PATENT DOCUMENTS

| | | | | |
|---|---|---|---|---|
| 2008/0260731 | A1* | 10/2008 | Bernett .................... | A61P 37/00 424/133.1 |
| 2015/0079074 | A1* | 3/2015 | Garidel ................... | A61P 43/00 424/133.1 |

FOREIGN PATENT DOCUMENTS

| | | |
|---|---|---|
| WO | 2014/160490 | 10/2014 |
| WO | 2014/160495 | 10/2014 |
| WO | 2015/048520 | 4/2015 |
| WO | 2015/075201 | 5/2015 |
| WO | 2015/157286 | 10/2015 |

OTHER PUBLICATIONS

International Search Report and Written Opinion in PCT/EP2017/065819 dated Oct. 4, 2017.
International Preliminary Report on Patentability in PCT/EP2017/065819 dated Jan. 1, 2019.
Extended European Search Report in EP16176322.2 dated Dec. 14, 2015.
Anderson et al. "Expression of Human B Cell-Associated Antigens on Leukemias and Lymphomas: A Model of Human B Cell Differentiation" Blood 1984 63(6):1424-1433.
Cleland et al. "The Development of Stable Protein Formulations: A Close Look at Protein Aggregation, Deamidation, and Oxidation" Critical Reviews in Therapeutic Drug Carrier Systems 1993 10(4):307-377.
Cleland et al. "A Specific Molar Ratio of Stabilizer to Protein is Required for Storage Stability of a Lyophilized Monoclonal Antibody" Journal of Pharmaceutical Sciences 2001 90(3):310-321.
Connolly et al. "Protein Aggregation in Frozen Trehalose Formulation: Effects of Composition, Cooling Rate, and Storage Temperature" Pharmaceutics, Drug Delivery and Pharmaceutical Technology 2015 104:4170-4184.
Esteves et al. "Stabilisation of Immunoconjugates by trehalose" Biotechnology Letters 2000 22:417-420.
Grossbard et al. "Anti-B4-blocked ricin: a phase II trial of 7 day continuous infusion in patients with multiple myeloma" British Journal of Haematology 1998 102:509-515.
Jurczak et al. "Single-agent MOR208 salvage and maintenance therapy in a patient with refractory/relapsing diffuse large B-cell lymphoma: a case report" Journal of Medical Case reports 2016 10:123.
Loken et al. "Flow Cytometric Analysis of Human Bone Marrow. II. Normal B Lymphocyte Development" Blood 1987 70(5):1316-1324.
Nadler et al. "B4, a human B lymphocyte-associated antigen expressed on normal,mitogen-activated, and malignant B lymphocytes" The Journal of Immunology 1983 131:224-250.
Robak et al. "Emerging immunological drugs for chronic lymcytic leukemia" Expert Opinion on Emerging Drugs 2015 20(3):423-447.
Scheuermann, R.H. and Racila, E. "CD19 Antigen in Leukemia and Lymphoma Diagnosis and Immunotherapy" Leukemia & Lymphoma 1995 18(5-6):385-397.
Selva et al. "Trehalose Preserves the Integrity of Lyophilized Phycoerythrin-AntiHuman CD8 Antibody Conjugates and Enhances their Thermal Stability in Flow Cytometric Assays" Journal of Pharmaceutical Sciences 2013 102(2): 649-659.
Treon et al. "Expression of Serotherapy Target Antigens in Waldenstrom's Macroglobulinemia: Therapeutic Applications and Conisderations" Seminars in Oncology 2003 30(2):248-252.
Uckun et al. "Detailed Studies on Expression and FUcntion of CD19 Surface Determinant by Using B43 Monoclonal Antibody and the Clinical Potential of Anti-CD19 Immunotoxin" Blood 1988 71(1):13-29.

(Continued)

*Primary Examiner* — Gary B Nickol
*Assistant Examiner* — Jegatheesan Seharaseyon
(74) *Attorney, Agent, or Firm* — Licata & Tyrrell P.C.

(57) ABSTRACT

The present disclosure describes a pharmaceutical formulation of an anti-CD19 antibody.

12 Claims, 2 Drawing Sheets

Specification includes a Sequence Listing.

(56) References Cited

OTHER PUBLICATIONS

Woyach et al. "A phase 1 trial of the Fc-engineered CD19 antibody XmAb5574 (MOR0208) demonstrates safety and preliminary efficacy in relapsed CLL" Blood 2014 124(24):3553-3560.

Zhou et al. "Formation of Stable Nanobubbles on Reconstituting Lyophilized Formulations Containing Trehalose" Journal of Pharmaceutical Sciences 2016 105:2240-2253.

Zhou et al. "Reduced Subvisible Particle Formation in Lyophilized Intravenous Immunoglobulin Formulations Contaning Polysorbate 20" Journal of Pharmaceutical Sciences 2016 105:2302-2309.

* cited by examiner

Figure 1

The amino acid sequence of the MOR208 HCDR1 is: SYVMH (SEQ ID NO: 1)

The amino acid sequence of the MOR208 HCDR2 is: NPYNDG (SEQ ID NO: 2)

The amino acid sequence of the MOR208 HCDR3 is: GTYYYGTRVFDY (SEQ ID NO: 3)

The amino acid sequence of the MOR208 LCDR1 is: RSSKSLQNVNGNTYLY (SEQ ID NO: 4)

The amino acid sequence of the MOR208 LCDR2 is: RMSNLNS (SEQ ID NO: 5)

The amino acid sequence of the MOR208 LCDR3 is: MQHLEYPIT (SEQ ID NO: 6)

The amino acids sequence of the MOR208 heavy chain Fc region is:

ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPDVFLFPPKPK
DTLMISRTPEVTCVVVDVSHEDPEVQFNWYVDGVEVHNAKTKPREEQFNSTFRVVSVLTVVHQD
WLNGKEYKCKVSNKALPAPEEKTISKTKGQPREPQVYTLPPSREEMTKNQVSLTCLVKGFYPSDIA
VEWESNGQPENNYKTTPPMLDSDGSFFLYSKLTVDKSRWQQGNVFSCSVMHEALHNHYTQKSL
SLSPGK (SEQ ID NO: 8).

The amino acids sequence of the MOR208 light chain Fc region is:

RTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC (SEQ ID NO: 9)

The amino acid sequence of the MOR208 Variable Heavy Domain is (CDRs are bolded and underlined):

EVQLVESGGGLVKPGGSLKLSCAASGYTFTSYVMHWVRQAPGKGLEWIGYINPYNDGTKYNEKF
QGRVTISSDKSISTAYMELSSLRSEDTAMYYCARGTYYYGTRVFDYWGQGTLVTVSS
(SEQ ID NO: 10)

The amino acid sequence of the MOR208 Variable Light Domain is (The CDRs are bolded and underlined):

DIVMTQSPATLSLSPGERATLSCRSSKSLQNVNGNTYLYWFQQKPGQSPQLLIYRMSNLNSGVPD
RFSGSGSGTEFTLTISSLEPEDFAVYYCMQHLEYPITFGAGTKLEIK (SEQ ID NO: 11)

SEQUENCE LISTING

<160> NUMBER OF SEQ ID NOS: 11

<210> SEQ ID NO 1
<211> LENGTH: 5
<212> TYPE: PRT
<213> ORGANISM: Artificial sequence
<220> FEATURE:
<223> OTHER INFORMATION: synthetic construct

<400> SEQUENCE: 1

Ser Tyr Val Met His
1               5

<210> SEQ ID NO 2
<211> LENGTH: 6
<212> TYPE: PRT
<213> ORGANISM: Artificial sequence

```
<220> FEATURE:
<223> OTHER INFORMATION: synthetic construct

<400> SEQUENCE: 2

Asn Pro Tyr Asn Asp Gly
1               5

<210> SEQ ID NO 3
<211> LENGTH: 12
<212> TYPE: PRT
<213> ORGANISM: Artificial sequence
<220> FEATURE:
<223> OTHER INFORMATION: synthetic construct

<400> SEQUENCE: 3

Gly Thr Tyr Tyr Tyr Gly Thr Arg Val Phe Asp Tyr
1               5                   10

<210> SEQ ID NO 4
<211> LENGTH: 16
<212> TYPE: PRT
<213> ORGANISM: Artificial sequence
<220> FEATURE:
<223> OTHER INFORMATION: synthetic construct

<400> SEQUENCE: 4

Arg Ser Ser Lys Ser Leu Gln Asn Val Asn Gly Asn Thr Tyr Leu Tyr
1               5                   10                  15

<210> SEQ ID NO 5
<211> LENGTH: 7
<212> TYPE: PRT
<213> ORGANISM: Artificial sequence
<220> FEATURE:
<223> OTHER INFORMATION: synthetic construct

<400> SEQUENCE: 5

Arg Met Ser Asn Leu Asn Ser
1               5

<210> SEQ ID NO 6
<211> LENGTH: 9
<212> TYPE: PRT
<213> ORGANISM: Artificial sequence
<220> FEATURE:
<223> OTHER INFORMATION: synthetic construct

<400> SEQUENCE: 6

Met Gln His Leu Glu Tyr Pro Ile Thr
1               5

<210> SEQ ID NO 7
<211> LENGTH: 556
<212> TYPE: PRT
<213> ORGANISM: Homo sapiens
<220> FEATURE:
<223> OTHER INFORMATION: CD19

<400> SEQUENCE: 7

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45
```

-continued

```
Gln Leu Thr Trp Ser Arg Glu Ser Pro Leu Lys Pro Phe Leu Lys Leu
     50                  55                  60

Ser Leu Gly Leu Pro Gly Leu Gly Ile His Met Arg Pro Leu Ala Ile
 65                  70                  75                  80

Trp Leu Phe Ile Phe Asn Val Ser Gln Gln Met Gly Gly Phe Tyr Leu
                 85                  90                  95

Cys Gln Pro Gly Pro Ser Glu Lys Ala Trp Gln Pro Gly Trp Thr
                100                 105                 110

Val Asn Val Glu Gly Ser Gly Glu Leu Phe Arg Trp Asn Val Ser Asp
             115                 120                 125

Leu Gly Gly Leu Gly Cys Gly Leu Lys Asn Arg Ser Ser Glu Gly Pro
        130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
        370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
```

```
            465                 470                 475                 480
Pro His Gly Ser Ala Trp Asp Pro Ser Arg Glu Ala Thr Ser Leu Gly
                    485                 490                 495

Ser Gln Ser Tyr Glu Asp Met Arg Gly Ile Leu Tyr Ala Ala Pro Gln
                500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
        530                 535                 540

Gly Gly Gly Gly Arg Met Gly Thr Trp Ser Thr Arg
545                 550                 555
```

<210> SEQ ID NO 8
<211> LENGTH: 330
<212> TYPE: PRT
<213> ORGANISM: Artificial sequence
<220> FEATURE:
<223> OTHER INFORMATION: synthetic construct

<400> SEQUENCE: 8

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
```

```
                275                 280                 285
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 107
<212> TYPE: PRT
<213> ORGANISM: Artificial sequence
<220> FEATURE:
<223> OTHER INFORMATION: synthetic construct

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 10
<211> LENGTH: 121
<212> TYPE: PRT
<213> ORGANISM: Artificial sequence
<220> FEATURE:
<223> OTHER INFORMATION: synthetic construct

<400> SEQUENCE: 10

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser
            115                 120

<210> SEQ ID NO 11
<211> LENGTH: 112
```

```
<212> TYPE: PRT
<213> ORGANISM: Artificial sequence
<220> FEATURE:
<223> OTHER INFORMATION: synthetic construct

<400> SEQUENCE: 11

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
                100                 105                 110
```

ANTI-CD19 ANTIBODY FORMULATIONS

This patent application is the National Stage of International Application No. PCT/EP2017/065819 filed Jun. 27, 2017, which claims the benefit of priority from EP 16176322.2 filed Jun. 27, 2016, each of which is incorporated by reference in its entirety.

FIELD OF THE INVENTION

The present disclosure is related to stable lyophilized pharmaceutical formulations of an anti-CD19 antibody and provides methods of making and methods of using such formulations.

BACKGROUND

B cells are lymphocytes that play a large role in the humoral immune response. They are produced in the bone marrow of most mammals, and represent 5-15% of the circulating lymphoid pool. The principal function of B cells is to make antibodies against various antigens, and are an essential component of the adaptive immune system.

Because of their critical role in regulating the immune system, disregulation of B cells is associated with a variety of disorders, such as lymphomas, and leukemias. These include non-Hodgkin's lymphoma (NHL), chronic lymphocytic leukemia (CLL) and acute lymphoblastic leukemia (ALL).

The human CD19 molecule is a structurally distinct cell surface receptor expressed on the surface of human B cells, including, but not limited to, pre-B cells, B cells in early development {i.e., immature B cells), mature B cells through terminal differentiation into plasma cells, and malignant B cells. CD 19 is expressed by most pre-B acute lymphoblastic leukemias (ALL), non-Hodgkin's lymphomas, B cell chronic lymphocytic leukemias (CLL), pro-lymphocytic leukemias, hairy cell leukemias, common acute lymphocytic leukemias, and some Null-acute lymphoblastic leukemias (Nadler et al, J. Immunol., 131:244-250 (1983), Loken et al, Blood, 70:1316-1324 (1987), Uckun et al, Blood, 71:13-29 (1988), Anderson et al, 1984. Blood, 63:1424-1433 (1984), Scheuermann, Leuk. Lymphoma, 18:385-397(1995)). The expression of CD19 on plasma cells further suggests it may be expressed on differentiated B cell tumors such as multiple myeloma, plasmacytomas, Waldenstrom's tumors (Grossbard et al., Br. J. Haematol, 102:509-15(1998); Treon et al, Semin. Oncol, 30:248-52(2003)).

Therefore, the CD 19 antigen is a target for immunotherapy in the treatment of non-Hodgkin's lymphoma (including each of the subtypes described herein), chronic lymphocytic leukemia and/or acute lymphoblastic leukemia.

MOR208 (previously named XmAb5574) is an Fc engineered humanized monoclonal antibody that binds CD19. The increase in binding of MOR208 Fc to FcγR, due to XmAb engineered mutations, significantly enhances in-vitro antibody dependent cell-mediated cytotoxicity (ADCC), antibody dependent cell-mediated phagocytosis (ADCP), and direct cytotoxic effects (apoptosis) on tumor relative to the unmodified antibody. MOR208 has not been shown to mediate complement dependent cytotoxicity.

MOR208 has or is currently being studied in clinical trials in CLL, ALL and NHL. Specifically, a Phase I trial titled Safety and Tolerability of XmAb®5574 in Chronic Lymphocytic Leukemia, and a Phase IIa trial titled Study of Fc-Optimized Anti-CD19 Antibody (MOR208) to treat B-cell Acute Lymphoblastic Leukemia (B-ALL) are completed. A Phase IIa trial titled Study of Fc-Optimized Anti-CD19 Antibody (MOR208) to Treat Non-Hodgkin's Lymphoma (NHL) has completed recruitment. And the following trials are ongoing: a Phase II/111 trial titled A Trial to Evaluate the Efficacy and Safety of MOR208 With Bendamustine (BEN) Versus Rituximab (RTX) With BEN in Adult Patients With Relapsed or Refractory Diffuse Large B-cel Lymphoma (DLBCL) (B-MIND), a Phase II trial titled Study to Evaluate Efficacy and Safety of MOR208 With Idelalisib in R/R CLL/SLL Patients Pretreated With BTKi, a Phase II trial titled A Study to Evaluate the Safety and Efficacy of Lenalidomide With MOR208 in Patients With R-R DLBCL, and a Phase II trial titled Phase II MOR208 in Combination With Lenalidomide for Patients With Relapsed or Refractory CLL, SLL or PLL or Older Patients With Untreated CLL, SLL or PLL.

Therapeutic antibodies and antibody fragments are large and more complex molecules than traditional organic and inorganic drugs small molecules as antibodies possess multiple functional groups in addition to complex three-dimensional structures and, therefore, the formulation of such proteins poses special challenges. For a protein to remain biologically active, a formulation must preserve the conformational integrity of at least a core sequence of the protein's amino acids while at the same time protecting the protein's multiple functional groups from degradation. Formulations of antibodies may have short shelf lives and the formulated antibodies may lose biological activity resulting from chemical and physical instabilities during storage. The three most common pathways for protein degradation are protein aggregation, deamidation and oxidation (Cleland et al., Critical Reviews in Therapeutic Drug Carrier Systems 10(4): 307-377 (1993)). In particular, aggregation can potentially lead to increased immune response in patients, leading to safety concerns and must be minimised or prevented.

SUMMARY OF THE INVENTION

It is an object of the invention to provide formulations of anti-CD19 antibodies, and in particular formulations of anti-CD19 antibodies having a suitable shelf life.

Suitable formulations for therapeutic antibodies can be an aqueous pharmaceutical composition or a lyophilisate which can be reconstituted to provide a solution for administration to a patient.

Provided herein are lyophilized pharmaceutical formulations comprising an antibody. In an aspect, the formulation comprises an anti-CD19 antibody, a buffer, sucrose, and a surfactant, wherein the formulation has a pH of about 6.0 wherein said anti-CD19 antibody comprises a heavy chain constant domain of the sequence ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPDVFLFPPKPKDTLMISRTPEVTCVVVDVSHEDPEVQFNWYVDGVEVHNAKTKPREEQFNSTFRVVSVLTVVHQD WLNGKEYKCKVSNKALPAPEEKTISKTKGQPREPQVYTLPPSREEMTKNQVSLTCLVKGFYPSDIA VEWESNGQPENNYKTTPPMLDSDGSFFLYSKLTVDKSRWQQGNVFSCSVMHEALHNHYTQKSLSLSPGK (SEQ ID NO: 8) and a light chain constant domain of the sequence RTVAAPSVFIFPPSDEQLKSGTASVVCLLNNFYPREAKVQWKVD- NALQSGNSQESVTEQDSKD STYSLSSTLTL-
SKADYEKHKVYACEVTHQGLSSPVTKSFNRGEC.
(SEQ ID NO: 9).

In one aspect, provided herein is a stable lyophilized pharmaceutical formulation, the formulation comprising an anti-CD19 antibody in a concentration of about 20 mg/ml to about 125 mg/ml, a buffer, polysorbate in a concentration of about 0.005% (w/v) to about 0.06% (w/v), and pH of about 6.0, wherein the formulation further comprises a) trehalose in a concentration of about 180 mM to about 240 mM
or
b) Mannitol in a concentration of about 180 mM to about 240 mM and Sucrose in a concentration of about 10 mM to about 50 mM.

In some embodiments, said anti-CD19 antibody comprises an HCDR1 region comprising of sequence SYVMH (SEQ ID NO: 1), an HCDR2 region comprising of sequence NPYNDG (SEQ ID NO: 2), an HCDR3 region comprising of sequence GTYYYGTRVFDY (SEQ ID NO: 3), an LCDR1 region comprising of sequence RSSKSLQNVNG-NTYLY (SEQ ID NO: 4), an LCDR2 region comprising of sequence RMSNLNS (SEQ ID NO: 5), and an LCDR3 region comprising of sequence MQHLEYPIT (SEQ ID NO: 6).

In some embodiments, said anti-CD19 antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In some embodiments, said anti-CD19 antibody comprises a variable heavy chain of the sequence EVQLVES-GGGLVKPGGSLKLSCAASGYTFT-
SYVMHWVRQAPGKGLEWIGYINPYNDGTKYNEKF
QGRVTISSDKSISTAYMELSSLRSEDTAMYY-
CARGTYYYGTRVFDYWGQGTLVTVSS (SEQ ID NO: 10) and a variable light chain of the sequence DIVMTQSPATLSLSPGERATLSCRSSKSLQNVNGNTY-
LYWFQQKPGQSPQLLIYRMSNLNSGVPD
RFSGSGSGTEFTLTISSLEPEDFAVYYCMQHLEYP-
ITFGAGTKLEIK (SEQ ID NO: 11).

In some embodiments, said anti-CD19 antibody comprises a heavy chain constant domain of the sequence ASTKGPSVFPLAPSSKSTSGGTAALGCLVKDYF-
PEPVTVSWNSGALTSGVHTFPAVLQSSGLYSL
SSVVTVPSSSLGTQTYICNVNHKPSNTKVDKKVE-
PKSCDKTHTCPPCPAPELLGGPDVFLFPPKPK
DTLMISRTPEVTCVVVDVSHEDPE-
VQFNWYVDGVEVHNAKTKPREEQFN-
STFRVVSVLTVVHQD WLNGKEYKCKVSNKALPAP-
EEKTISKTKGQPREPQVYTLPPSREEMTKNQVSLTC
LVKGFYPSDIA VEWESNGQPEN-
NYKTTPPMLDSDGSFFLYSK-
LTVDKSRWQQGNVFSCSVMHEALHNHYTQKSL
SLSPGK (SEQ ID NO: 8) and a light chain constant domain of the sequence RTVAAPSVFIFPPSDEQLKSG-
TASVVCLLNNFYPREAKVQWKVD-
NALQSGNSQESVTEQDSKD STYSLSSTLTL-
SKADYEKHKVYACEVTHQGLSSPVTKSFNRGEC.
(SEQ ID NO: 9).

In some embodiments, the anti-CD19 antibody in the formulation has a concentration of about 20 mg/ml to about 80 mg/ml. In some embodiments, the anti-CD19 antibody in the formulation has a concentration of about 40 mg/ml.

In some embodiments, said buffer in the formulation is citrate buffer or phosphate buffer.

In some embodiments, said trehalose in the formulation is about 200 mM. In some embodiments, said trehalose in the formulation is 200 mM.

In some embodiments, said Mannitol in the formulation is about 219 mM and Sucrose in the formulation is about 29 mM. In some embodiments, said Mannitol in the formulation is 219 mM and Sucrose in the formulation is 29 mM.

In some embodiments, the formulation has a pH of about 6.0. In some embodiments, the formulation has a pH of 6.0.

In some embodiments, said polysorbate in the formulation is polysorbate 20. In some embodiments, said polysorbate (e.g., polysorbate 20) in the formulation is of about 0.005% (w/v) to about 0.06% (w/v). In some embodiments, said polysorbate (e.g., polysorbate 20) in the formulation is about 0.02% (w/v). In some embodiments, said polysorbate (e.g., polysorbate 20) in the formulation is 0.02% (w/v).

In a further aspect, provided herein is a stable lyophilized pharmaceutical formulation, the formulation comprising an anti-CD19 antibody in a concentration of about 40 mg/ml, citrate in a concentration of about 25 mM, trehalose in a concentration of about 200 mM, polysorbate in a concentration of about 0.02% (w/v), and a pH of about 6.0.

In a further aspect, provided herein is a stable lyophilized pharmaceutical formulation, the formulation comprising an anti-CD19 antibody in a concentration of 40 mg/ml, citrate in a concentration of 25 mM, trehalose in a concentration of 200 mM, polysorbate in a concentration of 0.02% (w/v), and a pH of 6.0.

In a further aspect, provided herein is a stable lyophilized pharmaceutical formulation, the formulation comprising an anti-CD19 antibody in a concentration of about 40 mg/ml, citrate in a concentration of about 25 mM, Mannitol in a concentration of about 219 mM, Sucrose in a concentration of about 29 mM, polysorbate in a concentration of about 0.02% (w/v), and a pH of about 6.0.

In a further aspect, provided herein is a stable lyophilized pharmaceutical formulation, the formulation comprising an anti-CD19 antibody in a concentration of 40 mg/ml, citrate in a concentration of 25 mM, Mannitol in a concentration of 219 mM, Sucrose in a concentration of 29 mM, polysorbate in a concentration of 0.02% (w/v), and a pH of 6.0.

In some embodiments, said anti-CD19 antibody in the formulation is not subject to prior lyophilization, e.g. is liquid In some embodiments, said anti-CD19 antibody in the formulation is a monoclonal antibody. In some embodiments, said anti-CD19 antibody in the formulation is a full length antibody. In some embodiments, said anti-CD19 antibody in the formulation is an IgG antibody. In some embodiments, said anti-CD19 antibody in the formulation is a humanized or a human antibody. In some embodiments, said anti-CD19 antibody in the formulation is an antibody fragment comprising an antigen-binding region. In some embodiments, the antibody fragment is a Fab or F(ab')2 fragment.

DESCRIPTION OF DRAWINGS

FIG. 1: Provided are the amino acid sequences of MOR208.

DETAILED DESCRIPTION OF THE INVENTION

Figure 2:
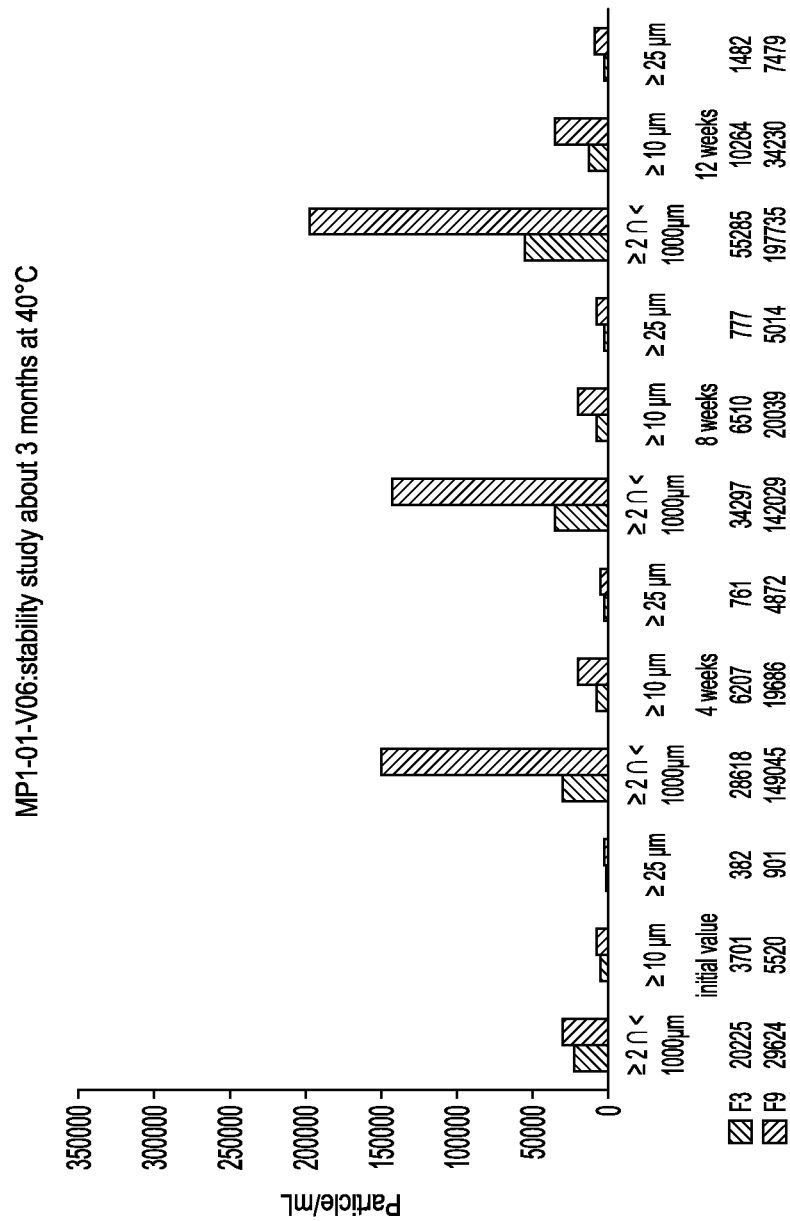
FIG. 2: Subvisible particle (SVP) count of MOR208 after 3 months at 40° C. Formulation 3 and Formulation 9 were compared and the mannitol/sucrose formulation generated more particles over time especially in the range between 2 μm and 1000 μm.

The term "antibody" means monoclonal antibodies, including any isotype, such as, IgG, IgM, IgA, IgD and IgE. An IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are referred to as CDR1, CDR2, and CDR3, numbered sequentially from the N-terminus. The more highly conserved portions of the variable regions outside of the CDRs are called the "framework regions". An "antibody fragment" means an Fv, scFv, dsFv, Fab, Fab' F(ab')2 fragment, or other fragment, which contains at least one variable heavy or variable light chain, each containing CDRs and framework regions.

"VH" refers to the variable region of an immunoglobulin heavy chain of an antibody, or antibody fragment. "VL" refers to the variable region of the immunoglobulin light chain of an antibody, or antibody fragment.

The term "CD19" refers to the protein known as CD19, having the following synonyms: B4, B-lymphocyte antigen CD19, B-lymphocyte surface antigen B4, CVID3, Differentiation antigen CD19, MGC12802, and T-cell surface antigen Leu-12.

Human CD19 has the amino acid sequence of:

```
                                       (SEQ ID NO: 7)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRFFKVTPPPGSGPQNQYGN

VLSLPTPTSGLGRAQRWAAGLGGTAPSYGNPSSDVQADGALGSRSPPGVG

PEEEEGEGYEEPDSEEDSEFYENDSNLGQDQLSQDGSGYENPEDEPLGPE

DEDSFSNAESYENEDEELTQPVARTMDFLSPHGSAWDPSREATSLGSQSY

EDMRGILYAAPQLRSIRGQPGPNHEEDADSYENMDNPDGPDPAWGGGRM

GTWSTR.
```

"MOR208" is an anti-CD19 antibody. The amino acid sequence of the variable domains is provided in FIG. 1. The amino acid sequence of the heavy and light chain Fc regions of MOR208 are provided in FIG. 1. "MOR208" and "XmAb 5574" are used as synonyms to describe the antibody shown in FIG. 1. The MOR208 antibody is described in U.S. patent application Ser. No. 12/377,251, which is incorporated by reference in its entirety.

Additional antibodies specific for CD19 are described in U.S. Pat. No. 7,109,304 (Immunomedics), which is incorporated by reference in its entirety; U.S. application Ser. No. 11/917,750 (Medarex), which is incorporated by reference in its entirety; U.S. application Ser. No. 11/852,106 (Medimmune), which is incorporated by reference in its entirety; U.S. application Ser. No. 11/648,505 (Merck Patent GmbH), which is incorporated by reference in its entirety; U.S. Pat. No. 7,968,687 (Seattle Genetics), which is incorporated by reference in its entirety; and U.S. application Ser. No. 12/710,442 (Glenmark Pharmaceuticals), which is incorporated by reference in its entirety.

In addition further antibodies specific for CD19 are described in WO2005012493 (U.S. Pat. No. 7,109,304), WO2010053716 (U.S. Ser. No. 12/266,999) (Immunomedics); WO2007002223 (US U.S. Pat. No. 8,097,703) (Medarex); WO2008022152 (Ser. No. 12/377,251) and WO2008150494 (Xencor), WO2008031056 (U.S. Ser. No. 11/852,106) (Medimmune); WO 2007076950 (U.S. Ser. No. 11/648,505) (Merck Patent GmbH); WO 2009/052431 (U.S. Ser. No. 12/253,895) (Seattle Genetics); and WO2010095031 (Ser. No. 12/710,442) (Glenmark Pharmaceuticals), WO2012010562 and WO2012010561 (International Drug Development), WO2011147834 (Roche Glycart), and WO 2012/156455 (Sanofi), which are all incorporated by reference in their entireties.

The term "pharmaceutical formulation" refers to a preparation for administration to subjects. Such subjects may be humans.

A "stable" formulation is one that can be administered to patients after storage. In aspects, the formulation essentially retains its physical and chemical properties, as well as its biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example.

Stability can be evaluated qualitatively and/or quantitatively in a variety of different ways, including evaluation of aggregate formation (for example using size exclusion chromatography, by measuring turbidity, and/or by visual inspection); by assessing charge heterogeneity using ion exchange chromatography (IEC), size exclusion chromatography (HP-SEC), SDS-PAGE analysis to compare reduced and intact antibody; evaluating biological activity or antigen binding function of the antibody; etc. Instability may involve any one or more of: aggregation, deamidation (e.g. Asn deamidation), oxidation (e.g. Met oxidation), isomerization (e.g. Asp isomerization), clipping/hydrolysis/fragmentation (e.g. hinge region fragmentation), succinimide formation, unpaired cysteine(s), N-terminal extension, C-terminal processing, glycosylation differences, etc.

As used herein, "biological activity" of a monoclonal antibody refers to the ability of the antibody to bind to antigen. It can further include antibody binding to antigen and resulting in a measurable biological response which can be measured in vitro or in vivo.

As used herein, "buffer" refers to a buffered solution that resists changes in pH by the action of its acid-base conjugate components. The buffer of this invention preferably has a pH in the range from about 4.5 to about 7.0, preferably from about 5.6 to about 7.0. In one embodiment the buffer has a pH of about 6.0 or a pH of 6.0. For example, a citrate buffer or a phosphate buffer are each an example of buffers that will control the pH in this range.

As used herein, a "surfactant" refers to a surface-active agent. Preferably the surfactant is a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetylbetaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc.); etc. In one embodiment, the surfactant herein is polysorbate 20.

"Fc region" means the constant region of an antibody, which in humans may be of the IgG1, 2, 3, 4 subclass or others. The sequences of human Fc regions are available at IMGT, Human IGH C-REGIONs, http://www.imgt.org/IMGTrepertoire/Proteins/protein/human/IGH/IGHC/Hu_GH-Callgenes.html (retrieved on 16 May 2011).

"Administered" or "administration" includes but is not limited to delivery by an injectable form, such as, for example, an intravenous, intramuscular, intradermal or subcutaneous route or mucosal route, for example, as a nasal spray or aerosol for inhalation or as an ingestable solution, capsule or tablet.

A "therapeutically effective amount" of a compound or combination refers to an amount sufficient to at least partially arrest the clinical manifestations of a given disease or disorder and its complications. The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist.

The "CDRs" herein are defined by either Chothia et al or Kabat et al. See Chothia C, Lesk AM. (1987) Canonical structures for the hypervariable regions of immunoglobulins. J Mol Biol., 196(4):901-17, which is incorporated by reference in its entirety. See Kabat E. A, Wu T. T., Perry H. M., Gottesman K. S. and Foeller C. (1991). Sequences of Proteins of Immunological Interest. 5th edit, NIH Publication no. 91-3242, US Dept. of Health and Human Services, Washington, D.C., which is incorporated by reference in its entirety.

"Cross competes" means the ability of an antibody or other binding agent to interfere with the binding of other antibodies or binding agents to CD19 in a standard competitive binding assay. The ability or extent to which an antibody or other binding agent is able to interfere with the binding of another antibody or binding molecule to CD19, and, therefore whether it can be said to cross-compete according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in International Patent Application No. WO 2003/48731

The term "epitope" includes any protein determinant capable of specific binding to an antibody or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational". The term "linear epitope" refers to an epitope with all of the points of interaction between the protein and the interacting molecule (such as an antibody) occur linearly along the primary amino acid sequence of the protein (continuous). The term "conformational epitope" refers to an epitope in which discontinuous amino acids that come together in three dimensional conformation. In a conformational epitope, the points of interaction occur across amino acid residues on the protein that are separated from one another.

"Binds the same epitope as" means the ability of an antibody or other binding agent to bind to CD19 and having the same epitope as the exemplified antibody. The epitopes of the exemplified antibody and other antibodies to CD19 can be determined using standard epitope mapping techniques. Epitope mapping techniques, well known in the art include Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al, (1984) Proc. Natl. Acad. Sci. USA 8:3998-4002; Geysen et al, (1985) Proc. Natl. Acad. Sci. USA 82:78-182; Geysen et al, (1986) Mol. Immunol. 23:709-715. Similarly, conformational epitopes are readily identified by determining spatial conformation of amino acids such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al, (1981) Proc. Natl. Acad. Sci USA 78:3824-3828; for determining antigenicity profiles, and the Kyte-Doolittle technique, Kyte et al, (1982) J. Mol. Biol. 157: 105-132; for hydropathy plots.

EMBODIMENTS

In another embodiment, provided herein is a stable lyophilized pharmaceutical formulation, the formulation comprising an anti-CD19 antibody in a concentration of about 20 mg/ml to about 125 mg/ml, a buffer, polysorbate in a concentration of about 0.005% (w/v) to about 0.06% (w/v), and pH of about 6.0, wherein the formulation further comprises a) trehalose in a concentration of about 180 mM to about 240 mM or b) Mannitol in a concentration of about 180 mM to about 240 mM and Sucrose in a concentration of about 10 mM to about 50 mM.

In another embodiment, provided herein is a stable lyophilized pharmaceutical formulation, the formulation comprising an anti-CD19 antibody in a concentration of about 20 mg/ml to about 125 mg/ml, a citrate buffer or phosphate buffer, polysorbate in a concentration of about 0.005% (w/v) to about 0.06% (w/v), and pH of about 6.0, wherein the formulation further comprises a) trehalose in a concentration of about 180 mM to about 240 mM or b) Mannitol in a concentration of about 180 mM to about 240 mM and Sucrose in a concentration of about 10 mM to about 50 mM.

In some embodiments, said buffer in the formulation is in a concentration of 10 to 75 mM. In some embodiments, said buffer in the formulation is in a concentration of 20 to 50 mM. In some embodiments, said buffer in the formulation is in a concentration of 20 to 40 mM. In some embodiments, said buffer in the formulation is in a concentration of 20 to 30 mM. In some embodiments, said buffer in the formulation is in a concentration of about 25 mM. In some embodiments, said buffer in the formulation is in a concentration of 25 mM. In some embodiments, said buffer in the formulation is citrate buffer or phosphate buffer.

In some embodiments, said citrate buffer in the formulation is in a concentration of of 10 to 75 mM. In some embodiments, said citrate buffer in the formulation is in a concentration of 20 to 50 mM. In some embodiments, said citrate buffer in the formulation is in a concentration of 20 to 30 mM. In some embodiments, said citrate buffer in the formulation is in a concentration of about 25 mM. In some embodiments, said citrate buffer in the formulation is in a concentration of 25 mM.

In some embodiments, said phosphate buffer in the formulation is in a concentration of of 10 to 75 mM. In some embodiments, said phosphate buffer in the formulation is in a concentration of of 20 to 50 mM. In some embodiments, said phosphate buffer in the formulation is in a concentration of 20 to 30 mM. In some embodiments, said phosphate buffer in the formulation is in a concentration of about 25 mM. In some embodiments, said phosphate buffer in the formulation is in a concentration of 25 mM.

In another embodiment, provided herein is a stable lyophilized pharmaceutical formulation, the formulation comprising an anti-CD19 antibody in a concentration of about 20 mg/ml to about 125 mg/ml, a citrate buffer or phosphate buffer in a concentration of of 20 to 50 mM, polysorbate in a concentration of about 0.005% (w/v) to about 0.06% (w/v), and pH of about 6.0, wherein the formulation further comprises a) trehalose in a concentration of about 180 mM to about 240 mM or b) Mannitol in a concentration of about 180 mM to about 240 mM and Sucrose in a concentration of about 10 mM to about 50 mM.

In another embodiment, provided herein is a stable lyophilized pharmaceutical formulation, the formulation comprising an anti-CD19 antibody in a concentration of about 20 mg/ml to about 125 mg/ml, a citrate buffer or phosphate buffer in a concentration of about 25 mM, polysorbate in a concentration of about 0.005% (w/v) to about 0.06% (w/v), and pH of about 6.0, wherein the formulation further comprises a) trehalose in a concentration of about 180 mM to about 240 mM or b) Mannitol in a concentration of about 180 mM to about 240 mM and Sucrose in a concentration of about 10 mM to about 50 mM.

In another embodiment, provided herein is a stable lyophilized pharmaceutical formulation, the formulation comprising an anti-CD19 antibody in a concentration of about 20 mg/ml to about 125 mg/ml, a citrate buffer in a concentration of about 25 mM, polysorbate in a concentration of about 0.005% (w/v) to about 0.06% (w/v), and pH of about 6.0, wherein the formulation further comprises a) trehalose in a concentration of about 180 mM to about 240 mM or b) Mannitol in a concentration of about 180 mM to about 240 mM and Sucrose in a concentration of about 10 mM to about 50 mM.

In another embodiment, provided herein is a stable lyophilized pharmaceutical formulation, the formulation comprising an anti-CD19 antibody in a concentration of about 20 mg/ml to about 125 mg/ml, a phosphate buffer in a concentration of about 25 mM, polysorbate in a concentration of about 0.005% (w/v) to about 0.06% (w/v), and pH of about 6.0, wherein the formulation further comprises a) trehalose in a concentration of about 180 mM to about 240 mM or b) Mannitol in a concentration of about 180 mM to about 240 mM and Sucrose in a concentration of about 10 mM to about 50 mM.

In a further embodiment said anti-CD19 antibody is a full length antibody. In a further embodiment said anti-CD19 antibody is an IgGl, an IgG2, an IgG3 or an IgG4 antibody.

In another embodiment said anti-CD19 antibody is a humanized or a human antibody. In a further embodiment said anti-CD19 antibody is an antibody fragment comprising an antigen-binding region. In a further embodiment said antibody fragment is a Fab or F(ab')2 fragment.

In another embodiment said stable lyophilized pharmaceutical formulation is stable at 2-8° C. for at least 6 months, at least 12 months, at least 18 months, at least 24 months or at least 36 months.

In another embodiment said stable lyophilized pharmaceutical formulation is stable at about 40° C. for at least about 1, 2, 3, 4, 5, 6, 7, 8, 9, 10, 11, 12, 13, 14, 15, 16 or more weeks. In certain embodiments, said stable lyophilized pharmaceutical formulation is stable at about 40° C. for at least about 1, 2, 3, 4, 5 or more months. In certain embodiments, said stable lyophilized pharmaceutical formulation is stable at about 25° C. for at least 1, 2, 3, 4, 5, 6, 7, 8, 9, 10, 11, 12 or more months. In certain embodiments, said stable lyophilized pharmaceutical formulation is stable at about 5° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments, said stable lyophilized pharmaceutical formulation is stable at about 5+/−3° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments, said stable lyophilized pharmaceutical formulation is stable at about −20° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments, said stable lyophilized pharmaceutical formulation is stable at 5° C. or −20° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months.

In a further embodiment the anti-CD19 antibody in the formulation retains at least 60%, at least 70%, at least 80%, at least 90%, at least 95% of its biological activity after storage. In some embodiment the biological activity is measured by antibody binding to CD19. In some embodiment the biological activity is measured by antibody binding to CD19 in a FACS CD19 binding assay. In some embodiment the biological activity is measured by ADCC activity of said anti-CD19 antibody.

In some embodiment stable lyophilized pharmaceutical formulation is sterile.

In a further embodiment said stable lyophilized pharmaceutical formulation is suitable to be administered to a subject. In a further embodiment said said stable lyophilized pharmaceutical formulation is suitable for intravenous (IV) administration or subcutaneous administration.

In another aspect, provided herein is an article of manufacture comprising a container holding the stable lyophilized pharmaceutical formulation as disclosed herein. In an embodiment said container is a glass vial or a metal alloy container. In a further embodiment the metal alloy is 316L stainless steel or hastelloy.

In another aspect, provided herein is method of treating a disease or disorder in a subject comprising administering an effective amount of the formulation disclosed herein to the subject, wherein the disease or disorder is cancer. In another aspect, provided herein is the use of the stable lyophilized pharmaceutical formulation as disclosed herein for the treatment of a disease or disorder in a subject comprising administering an effective amount of said formulation to the subject, wherein the disease or disorder is cancer. In a further aspect, provided herein is the use of the stable lyophilized pharmaceutical formulation as disclosed herein for the manufacture of a medicament for the treatment of a disease or disorder in a subject comprising administering an effective amount of said formulation to the subject, wherein the disease or disorder is cancer. In an embodiment the disease or disorder is non-Hodgkin's lymphoma (including each the subtypes described herein), chronic lymphocytic leukemia and/or acute lymphoblastic leukemia. In embodiments, the non-Hodgkin's lymphoma is selected from the group consisting of follicular lymphoma, small lymphocytic lymphoma, mucosa-associated lymphoid tissue, marginal zone, diffuse large B cell, Burkitt's, and mantle cell.

In some embodiments, provided herein is a stable lyophilized pharmaceutical formulation, the formulation comprising an anti-CD19 antibody in a concentration of about 20 mg/ml to about 125 mg/ml, a citrate buffer in a concentration of about 25 mM, polysorbate in a concentration of about 0.005% (w/v) to about 0.06% (w/v), and pH of about 6.0, wherein the formulation further comprises a) trehalose in a concentration of about 180 mM to about 240 mM
or
b) Mannitol in a concentration of about 180 mM to about 240 mM and Sucrose in a concentration of about 10 mM to about 50 mM,
wherein said anti-CD19 antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In some embodiments, provided herein is a stable lyophilized pharmaceutical formulation, the formulation comprising an anti-CD19 antibody in a concentration of about 20 mg/ml to about 125 mg/ml, a citrate buffer in a concentration of about 25 mM, polysorbate in a concentration of about 0.005% (w/v) to about 0.06% (w/v), and pH of about 6.0, wherein the formulation further comprises a) trehalose in a concentration of about 180 mM to about 240 mM
or
b) Mannitol in a concentration of about 180 mM to about 240 mM and Sucrose in a concentration of about 10 mM to about 50 mM, wherein said anti-CD19 antibody comprises a variable heavy chain of the sequence EVQLVESGGGLVKPGGSLKLSCAASGYTFTSYVMHWVRQAPGKGLEWIGYINPYNDGTKYNEKF QGRVTISSDKSISTAYMELSSLRSEDTAMYYCARGTYYYGTRVFDYW GQGTLVTVSS (SEQ ID NO: 10) and a variable light chain of the sequence DIVMTQSPATLSLSPGERATLSCRSSKSLQNVNGNTY-LYWFQQKPGQSPQLLIYRMSNLNSGVPD RFSGSGSGTEFTLTISSLEPEDFAVYYCMQHLEYPITFGAGTKLEIK (SEQ ID NO: 11).

In some embodiments, provided herein is a stable lyophilized pharmaceutical formulation, the formulation comprising an anti-CD19 antibody in a concentration of about 20 mg/ml to about 125 mg/ml, a citrate buffer in a concentration of about 25 mM, polysorbate in a concentration of about 0.005% (w/v) to about 0.06% (w/v), and pH of about 6.0, wherein the formulation further comprises a) trehalose in a concentration of about 180 mM to about 240 mM
or
b) Mannitol in a concentration of about 180 mM to about 240 mM and Sucrose in a concentration of about 10 mM to about 50 mM, wherein said anti-CD19 antibody comprises a heavy chain constant domain of the sequence ASTKGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPDVFLFPPKPK DTLMISRTPEVTCVVVDVSHEDPEVQFNWYVDGVEVHNAKTKPREEQFNSTFRVVSVLTVVHQD WLNGKEYKCKVSNKALPAPEEKTISKTKGQPREPQVYTLPPSREEMTKNQVSLTCL VKGFYPSDIA VEWESNGQPENNYKTTPPMLDSDGSFFLYSK-LTVDKSRWQQGNVFSCSVMHEALHNHYTQKSL SLSPGK (SEQ ID NO: 8) and a light chain constant domain of the sequence RTVAAPSVFIFPPSDEQLKSG-TASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises
  a) trehalose in a concentration of about 200 mM
or
  b) Mannitol in a concentration of about 219 mM and Sucrose in a concentration of about 29 mM, wherein said anti-CD19 antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises a) trehalose in a concentration of about 200 mM
or
b) Mannitol in a concentration of about 219 mM and Sucrose in a concentration of about 29 mM, wherein said anti-CD19 antibody comprises a variable heavy chain of the sequence EVQLVESGGGLVKPGGSLKLSCAASGYTFT-SYVMHWVRQAPGKGLEWIGYINPYNDGTKYNEKF QGRVTISSDKSISTAYMELSSLRSEDTAMYY-CARGTYYYGTRVFDYWGQGTLVTVSS (SEQ ID NO: 10) and a variable light chain of the sequence DIVMTQSPATLSLSPGERATLSCRSSKSLQNVNGNTY-LYWFQQKPGQSPQLLIYRMSNLNSGVPD RFSGSGSGTEFTLTISSLEPEDFAVYYCMQHLEYP-ITFGAGTKLEIK (SEQ ID NO: 11).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises
a) trehalose in a concentration of about 200 mM
or
b) Mannitol in a concentration of about 219 mM and Sucrose in a concentration of about 29 mM, wherein said anti-CD19 antibody comprises a heavy chain constant domain of the sequence ASTKGPSVFPLAPSSKSTSGGTAAL-GCLVKDYFPEPVTVSWNSGALTSGVHTFPAVLQSSG-LYSL SSVVTVPSSSLGTQTYICNVNHKPSNTKVDKKVE-PKSCDKTHTCPPCPAPELLGGPDVFLFPPKPK DTLMISRTPEVTCVVVDVSHEDPE-VQFNWYVDGVEVHNAKTKPREEQFN-STFRVVSVLTVVHQD WLNGKEYKCKVSNKALPAP-EEKTISKTKGQPREPQVYTLPPSREEMTKNQVSLTCL VKGFYPSDIA VEWESNGQPEN-NYKTTPPMLDSDGSFFLYSK-LTVDKSRWQQGNVFSCSVMHEALHNHYTQKSL SLSPGK (SEQ ID NO: 8) and a light chain constant domain of the sequence RTVAAPSVFIFPPSDEQLKSG-TASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises
a) trehalose in a concentration of about 200 mM
or
b) Mannitol in a concentration of about 219 mM and Sucrose in a concentration of about 29 mM, wherein said anti-CD19 antibody comprises a variable heavy chain having at least 85%, 86%, 87%, 89%, 90%, 91%, 92%, 93%, 94%, 95%, 96%, 97%, 98%, or 99% identity to the sequence EVQLVESGGGLVKPGGSLKLSCAASGYTFTSYVM HWVRQAPGKGLEWIGYINPYNDGTKYNEKF QGRVTISSDKSISTAYMELSSLRSEDTAMYY-CARGTYYYGTRVFDYWGQGTLVTVSS (SEQ ID NO: 10) and a variable light chain having at least 85%, 86%, 87%, 89%, 90%, 91%, 92%, 93%, 94%, 95%, 96%, 97%, 98%, or 99% identity to the sequence DIVMTQSPATLSL-SPGERATLSCRSSKSLQNVNGNTY-LYWFQQKPGQSPQLLIYRMSN LNSGVPD RFSGSGSGTEFTLTISSLEPEDFAVYYCMQHLEYP-ITFGAGTKLEIK (SEQ ID NO: 11).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises
a) trehalose in a concentration of about 200 mM
or
b) Mannitol in a concentration of about 219 mM and Sucrose in a concentration of about 29 mM, wherein said anti-CD19 antibody comprises a heavy chain constant domain having at least 85%, 86%, 87%, 89%, 90%, 91%, 92%, 93%, 94%, 95%, 96%, 97%, 98%, or 99% identity to the sequence ASTKGPSVFPLAPSSKSTSGGTAALGCLVKDYF-PEPVTVSWNSGALTSGVHTFPAVLQSSGLYSL SSVVTVPSSSLGTQTYICNVNHKPSNTKVDKKVE-PKSCDKTHTCPPCPAPELLGGPDVFLFPPKPK DTLMISRTPEVTCVVVDVSHEDPE-VQFNWYVDGVEVHNAKTKPREEQFN-STFRVVSVLTVVHQD WLNGKEYKCKVSNKALPAP-EEKTISKTKGQPREPQVYTLPPSREEMTKNQVSLTCL VKGFYPSDIA VEWESNGQPENNYKTTPPM LDSDGSFFLYSKLTVDKSRWQQGNVFSCSVMH EALHNHYTQKSL SLSPGK (SEQ ID NO: 8) and a light chain constant domain having at least 85%, 86%, 87%, 89%, 90%, 91%, 92%, 93%, 94%, 95%, 96%, 97%, 98%, or 99% identity to the sequence RTVAAPSVFIFPPSDEQLKSG-TASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises trehalose in a concentration of about 200 mM, wherein said anti-CD19 antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises Mannitol in a concentration of about 219 mM and Sucrose in a concentration of about 29 mM, wherein said anti-CD19 antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises trehalose in a concentration of about 200 mM wherein said anti-CD19 antibody comprises a variable heavy chain of the sequence EVQLVESGGGLVKPGGSLKLSCAASGYTFT-SYVMHWVRQAPGKGLEWIGYINPYNDGTKYNEKF QGRVTISSDKSISTAYMELSSLRSEDTAMYY-CARGTYYYGTRVFDYWGQGTLVTVSS (SEQ ID NO: 10) and a variable light chain of the sequence DIVMTQSPATLSLSPGERATLSCRSSKSLQNVNGNTY-LYWFQQKPGQSPQLLIYRMSNLNSGVPD RFSGSGSGTEFTLTISSLEPEDFAVYYCMQHLEYP-ITFGAGTKLEIK (SEQ ID NO: 11).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises Mannitol in a concentration of about 219 mM and Sucrose in a concentration of about 29 mM, wherein said anti-CD19 antibody comprises a variable heavy chain of the sequence EVQLVESGGGLVKPGGSLKLSCAASGYTFT-SYVMHWVRQAPGKGLEWIGYINPYNDGTKYNEKF QGRVTISSDKSISTAYMELSSLRSEDTAMYY-CARGTYYYGTRVFDYWGQGTLVTVSS (SEQ ID NO: 10) and a variable light chain of the sequence DIVMTQSPATLSLSPGERATLSCRSSKSLQNVNGNTY-LYWFQQKPGQSPQLLIYRMSNLNSGVPD RFSGSGSGTEFTLTISSLEPEDFAVYYCMQHLEYP-ITFGAGTKLEIK (SEQ ID NO: 11).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises trehalose in a concentration of about 200 mM, wherein said anti-CD19 antibody comprises a heavy chain constant domain of the sequence ASTKGPSVFPLAPSSKST-SGGTAALGCLVKDYFPEPVTVSWNSGALT-SGVHTFPAVLQSSGLYSL SSVVTVPSSSLGTQTYICNVNHKPSNTKVDKKVE-PKSCDKTHTCPPCPAPELLGGPDVFLFPPKPK DTLMISRTPEVTCVVVDVSHEDPE-VQFNWYVDGVEVHNAKTKPREEQFN-STFRVVSVLTVVHQD WLNGKEYKCKVSNKALPAP-EEKTISKTKGQPREPQVYTLPPSREEMTKNQVSLTCL VKGFYPSDIA VEWESNGQPEN-NYKTTPPMLDSDGSFFLYSK-LTVDKSRWQQGNVFSCSVMHEALHNHYTQKSL SLSPGK (SEQ ID NO: 8) and a light chain constant domain of the sequence RTVAAPSVFIFPPSDEQLKSG-TASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of about 40 mg/ml, a citrate buffer in a concentration of about 25 mM, polysorbate in a concentration of about 0.02% (w/v), and pH of about 6.0, wherein the formulation further comprises Mannitol in a concentration of about 219 mM and Sucrose in a concentration of about 29 mM, wherein said anti-CD19 antibody comprises a heavy chain constant domain of the sequence ASTKGPSVFPLAPSSKSTSGGTAAL-GCLVKDYFPEPVTVSWNSGALTSGVHTFPAVLQSSG-LYSL SSVVTVPSSSLGTQTYICNVNHKPSNTKVDKKVE-PKSCDKTHTCPPCPAPELLGGPDVFLFPPKPK DTLMISRTPEVTCVVVDVSHEDPE-VQFNWYVDGVEVHNAKTKPREEQFN-STFRVVSVLTVVHQD WLNGKEYKCKVSNKALPAP-EEKTISKTKGQPREPQVYTLPPSREEMTKNQVSLTCL VKGFYPSDIA VEWESNGQPEN-NYKTTPPMLDSDGSFFLYSK-LTVDKSRWQQGNVFSCSVMHEALHNHYTQKSL SLSPGK (SEQ ID NO: 8) and a light chain constant domain of the sequence RTVAAPSVFIFPPSDEQLKSG-TASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of about 40 mg/ml, a phosphate buffer in a concentration of 20 to 40 mM, polysorbate in a concentration of about 0.02% (w/v), and pH of about 6.0, wherein the formulation further comprises trehalose in a concentration of about 200 mM, wherein said anti-CD19 antibody comprises a heavy chain constant domain of the sequence ASTKGPSVF-PLAPSSKSTSGGTAALGCLVKDYF-PEPVTVSWNSGALTSGVHTFPAVLQSSGLYSL SSVVTVPSSSLGTQTYICNVNHKPSNTKVDKKVE-PKSCDKTHTCPPCPAPELLGGPDVFLFPPKPK DTLMISRTPEVTCVVVDVSHEDPE-VQFNWYVDGVEVHNAKTKPREEQFN-STFRVVSVLTVVHQD WLNGKEYKCKVSNKALPAP-EEKTISKTKGQPREPQVYTLPPSREEMTKNQVSLTCL VKGFYPSDIA VEWESNGQPEN-NYKTTPPMLDSDGSFFLYSK-LTVDKSRWQQGNVFSCSVMHEALHNHYTQKSL SLSPGK (SEQ ID NO: 8) and a light chain constant domain of the sequence RTVAAPSVFIFPPSDEQLKSG-TASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of about 40 mg/ml, a phosphate buffer in a concentration of 20 to 40 mM, polysorbate in a concentration of about 0.02% (w/v), and pH of about 6.0, wherein the formulation further comprises Mannitol in a concentration of about 219 mM and Sucrose in a concentration of about 29 mM, wherein said anti-CD19 antibody comprises a heavy chain constant domain of the sequence ASTKGPSVFPLAPSSKST-SGGTAALGCLVKDYFPEPVTVSWNSGALT-SGVHTFPAVLQSSGLYSL SSVVTVPSSSLGTQTYICNVNHKPSNTKVDKKVE-PKSCDKTHTCPPCPAPELLGGPDVFLFPPKPK DTLMISRTPEVTCVVVDVSHEDPE-VQFNWYVDGVEVHNAKTKPREEQFN-STFRVVSVLTVVHQD WLNGKEYKCKVSNKALPAP-EEKTISKTKGQPREPQVYTLPPSREEMTKNQVSLTCL VKGFYPSDIA VEWESNGQPEN-NYKTTPPMLDSDGSFFLYSK-LTVDKSRWQQGNVFSCSVMHEALHNHYTQKSL SLSPGK (SEQ ID NO: 8) and a light chain constant domain of the sequence RTVAAPSVFIFPPSDEQLKSG-TASVVCLLNNFYPREAKVQWKVD- NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of about 40 mg/ml, a phosphate buffer in a concentration of about 25 mM, polysorbate in a concentration of about 0.02% (w/v), and pH of about 6.0, wherein the formulation further comprises trehalose in a concentration of about 200 mM, wherein said anti-CD19 antibody comprises a heavy chain constant domain of the sequence ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPDVFLFPPKPKDTLMISRTPEVTCVVVDVSHEDPEVQFNWYVDGVEVHNAKTKPREEQFNSTFRVVSVLTVVHQD WLNGKEYKCKVSNKALPAPEEKTISKTKGQPREPQVYTLPPSREEMTKNQVSLTCL VKGFYPSDIA VEWESNGQPENNYKTTPPMLDSDGSFFLYSKLTVDKSRWQQGNVFSCSVMHEALHNHYTQKSL SLSPGK (SEQ ID NO: 8) and a light chain constant domain of the sequence RTVAAPSVFIFPPSDEQLKSGTASVVCLLNNFYPREAKVQWKVDNALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of about 40 mg/ml, a phosphate buffer in a concentration of about 25 mM, polysorbate in a concentration of about 0.02% (w/v), and pH of about 6.0, wherein the formulation further comprises Mannitol in a concentration of about 219 mM and Sucrose in a concentration of about 29 mM, wherein said anti-CD19 antibody comprises a heavy chain constant domain of the sequence ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPDVFLFPPKPKDTLMISRTPEVTCVVVDVSHEDPEVQFNWYVDGVEVHNAKTKPREEQFNSTFRVVSVLTVVHQD WLNGKEYKCKVSNKALPAPEEKTISKTKGQPREPQVYTLPPSREEMTKNQVSLTC LVKGFYPSDIA VEWESNGQPENNYKTTPPMLDSDGSFFLYSKLTVDKSRWQQGNVFSCSVMHEALHNHYTQKSL SLSPGK (SEQ ID NO: 8) and a light chain constant domain of the sequence RTVAAPSVFIFPPSDEQLKSGTASVVCLLNNFYPREAKVQWKVDNALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of 40 mg/ml, a citrate buffer in a concentration of 25 mM, polysorbate in a concentration of 0.02% (w/v), and pH of 6.0, wherein the formulation further comprises trehalose in a concentration of 200 mM, wherein said anti-CD19 antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In some embodiments, provided herein is a stable lyophilized pharmaceutical formulation, the formulation comprising an anti-CD19 antibody in a concentration of 40 mg/ml, a citrate buffer in a concentration of 25 mM, polysorbate in a concentration of 0.02% (w/v), and pH of 6.0, wherein the formulation further comprises Mannitol in a concentration of 219 mM and Sucrose in a concentration of 29 mM, wherein said anti-CD19 antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In some embodiments, provided herein is a stable lyophilized pharmaceutical formulation, the formulation comprising an anti-CD19 antibody in a concentration of 40 mg/ml, a citrate buffer in a concentration of 25 mM, polysorbate in a concentration of 0.02% (w/v), and pH of 6.0, wherein the formulation further comprises trehalose in a concentration of 200 mM wherein said anti-CD19 antibody comprises a variable heavy chain of the sequence EVQLVESGGGLVKPGGSLKLSCAASGYTFTSYVMHWVRQAPGKGLEWIGYINPYNDGTKYNEKF QGRVTISSDKSISTAYMELSSLRSEDTAMYYCARGTYYYGTRVFDYWGQGTLVTVSS (SEQ ID NO: 10) and a variable light chain of the sequence DIVMTQSPATLSLSPGERATLSCRSSKSLQNVNGNTY-LYWFQQKPGQSPQLLIYRMSNLNSGVPD RFSGSGSGTEFTLTISSLEPEDFAVYYCMQHLEYPITFGAGTKLEIK (SEQ ID NO: 11).

In some embodiments, provided herein is a stable lyophilized pharmaceutical formulation, the formulation comprising an anti-CD19 antibody in a concentration of 40 mg/ml, a citrate buffer in a concentration of 25 mM, polysorbate in a concentration of 0.02% (w/v), and pH of 6.0, wherein the formulation further comprises Mannitol in a concentration of 219 mM and Sucrose in a concentration of 29 mM, wherein said anti-CD19 antibody comprises a variable heavy chain of the sequence EVQLVESGGGLVKPGGSLKLSCAASGYTFTSYVMHWVRQAPGKGLEWIGYINPYNDGTKYNEKF QGRVTISSDKSISTAYMELSSLRSEDTAMYYCARGTYYYGTRVFDYWGQGTLVTVSS (SEQ ID NO: 10) and a variable light chain of the sequence DIVMTQSPATLSLSPGERATLSCRSSKSLQNVNGNTY-LYWFQQKPGQSPQLLIYRMSNLNSGVPD RFSGSGSGTEFTLTISSLEPEDFAVYYCMQHLEYPITFGAGTKLEIK (SEQ ID NO: 11).

In some embodiments, provided herein is a stable lyophilized pharmaceutical formulation, the formulation comprising an anti-CD19 antibody in a concentration of 40 mg/ml, a citrate buffer in a concentration of 25 mM, polysorbate in a concentration of 0.02% (w/v), and pH of 6.0, wherein the formulation further comprises trehalose in a concentration of 200 mM, wherein said anti-CD19 antibody comprises a heavy chain constant domain of the sequence ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPDVFLFPPKPKDTLMISRTPEVTCVVVDVSHEDPEVQFNWYVDGVEVHNAKTKPREEQFNSTFRVVSVLTVVHQD WLNGKEYKCKVSNKALPAP- EEKTISKTKGQPREPQVYTLPPSREEMTKNQVSLTCL VKGFYPSDIA VEWESNGQPENNYKTTPPM LDSDGSFFLYSKLTVDKSRWQQGNVFSCSVMH EALHNHYTQKSL SLSPGK (SEQ ID NO: 8) and a light chain constant domain of the sequence RTVAAPSVFIFPPS-DEQLKSGTASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of 40 mg/ml, a phosphate buffer in a concentration of 25 mM, polysorbate in a concentration of 0.02% (w/v), and pH of 6.0, wherein the formulation further comprises trehalose in a concentration of 200 mM, wherein said anti-CD19 antibody comprises a heavy chain constant domain of the sequence ASTKGPSVFPLAPSSKSTSGGTAAL-GCLVKDYFPEPVTVSWNSGALTSGVHTFPAVLQSSG-LYSL SSVVTVPSSSLGTQTYICNVNHKPSNTKVDKKVE-PKSCDKTHTCPPCPAPELLGGPDVFLFPPKPK DTLMISRTPEVTCVVVDVSHEDPE-VQFNWYVDGVEVHNAKTKPREEQFN-STFRVVSVLTVVHQD WLNGKEYKCKVSNKALPAP-EEKTISKTKGQPREPQVYTLPPSREEMTKNQVSLTCL VKGFYPSDIA VEWESNGQPEN-NYKTTPPMLDSDGSFFLYSK-LTVDKSRWQQGNVFSCSVMHEALHNHYTQKSL SLSPGK (SEQ ID NO: 8) and a light chain constant domain of the sequence RTVAAPSVFIFPPSDEQLKSG-TASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of 40 mg/ml, a citrate buffer in a concentration of 25 mM, polysorbate in a concentration of 0.02% (w/v), and pH of 6.0, wherein the formulation further comprises Mannitol in a concentration of 219 mM and Sucrose in a concentration of 29 mM, wherein said anti-CD19 antibody comprises a heavy chain constant domain of the sequence ASTKGPSVF-PLAPSSKSTSGGTAALGCLVKDYF-PEPVTVSWNSGALTSGVHTFPAVLQSSGLYSL SSVVTVPSSSLGTQTYICNVNHKPSNTKVDKKVE-PKSCDKTHTCPPCPAPELLGGPDVFLFPPKPK DTLMISRTPEVTCVVVDVSH EDPE-VQFNWYVDGVEVHNAKTKPREEQFN-STFRVVSVLTVVHQD WLNGKEYKCKVSNKALPAP-EEKTISKTKGQPREPQVYTLPPSREEMTKNQVSLTC LVKGFYPSDIA VEWESNGQPEN-NYKTTPPMLDSDGSFFLYSK-LTVDKSRWQQGNVFSCSVMHEALHNHYTQKSL SLSPGK (SEQ ID NO: 8) and a light chain constant domain of the sequence RTVAAPSVFIFPPSDEQLKSG-TASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

In some embodiments, provided herein is a stable lyophilized pharmaceutical formulation, the formulation comprising an anti-CD19 antibody in a concentration of 40 mg/ml, a phosphate buffer in a concentration of 25 mM, polysorbate in a concentration of 0.02% (w/v), and pH of 6.0, wherein the formulation further comprises Mannitol in a concentration of 219 mM and Sucrose in a concentration of 29 mM, wherein said anti-CD19 antibody comprises a heavy chain constant domain of the sequence ASTKGPSVF-PLAPSSKSTSGGTAALGCLVKDYF-PEPVTVSWNSGALTSGVHTFPAVLQSSGLYSL SSVVTVPSSSLGTQTYICNVNHKPSNTKVDKKVE-PKSCDKTHTCPPCPAPELLGGPDVFLFPPKPK DTLMISRTPEVTCVVVDVSHEDPE-VQFNWYVDGVEVHNAKTKPREEQFN-STFRVVSVLTVVHQD WLNGKEYKCKVSNKALPAP-EEKTISKTKGQPREPQVYTLPPSREEMTKNQVSLTCL VKGFYPSDIA VEWESNGQPEN-NYKTTPPMLDSDGSFFLYSK-LTVDKSRWQQGNVFSCSVMHEALHNHYTQKSL SLSPGK (SEQ ID NO: 8) and a light chain constant domain of the sequence RTVAAPSVFIFPPSDEQLKSG-TASVVCLLNNFYPREAKVQWKVD-NALQSGNSQESVTEQDSKD STYSLSSTLTL-SKADYEKHKVYACEVTHQGLSSPVTKSFNRGEC. (SEQ ID NO: 9).

WORKING EXAMPLES

Working Example 1: Biophysical Characterization of MOR208

The biophysical properties of MOR208 were analyzed for the purpose of characterization, preformulation-screening and high concentration feasibility.

To assess the structural stability of MOR208, thermal melting experiments using DSF (Differential Scanning Fluorimetry) and CD spectroscopy were acquired. MOR208 samples were diluted to a concentration of 1.1 mg/mL. The hydrophobic dye sypro-orange was added to detect unfolding of the protein and respective melting curves were generated. The samples showed a relatively low melting temperature of 47° C. indicated by a step increase in fluorescence.

MOR208 is a humanized monoclonal antibody binding to CD19 on B-cells and their progenitors. The Fc region has been engineered (S239D/I332E) to enhance the effector functions supporting B-cell depletion. According to the current working hypothesis this Fc region format leads to CH2 domain flexibility, which results in enhanced ADCC potency but may be accompanied with adecreased melting temperature of the Fc domain.

Furthermore a pH screening study was performed using DSC, RALS and ITF to identify the most stable pH range for the protein. A pH range from 3.5 to 8.0 was covered in the study. The measurements were executed in a mixed buffer system covering the desired pH range. The most stable pH range for MOR208 was identified between pH 6.0 and 7.0 based on the results obtained.

Therefore two buffer systems were identified which provide sufficient buffer capacity in the pH range between pH 6.0 and 7.0 and are phamaceutical acceptable for parenteral use:

Citrate (pH 5.5; 6.0)

Histidine (pH 6.0; 6.5; 7.0)

Further DSC, RALS and ITF measurements were executed to test the thermal stability of MOR208 in 25 mM Citrate and 25 mM Histidine buffer. Only Citrate at a pH of 5.5 showed significantly lower transition temperatures where all other tested samples showed a comparable, thermal stability. This conclusion was also confirmed by RALS and ITF testing.

Furthermore the impact of ionic strength, sugars, polyols and polysorbate 20 on the thermal stability of MOR208 was tested. 25 mM Citrate buffer at pH 6.0 was selected as a basic buffer system for the preparation of the samples containing NaCl or sugar or polysorbate 20. The measurements showed that the addition of NaCl increases the thermal stability of MOR208 based on the first transition temperature at 52° C. This observation was confirmed by ITF measurements. The results of the RALS testing did not identify any impact of NaCl on the thermal stability of MOR208.

The impact of sugars (trehalose and sucrose) and mannitol on the thermal stability of MOR208 was tested using concentrations of 200 mM for trehalose, 210 mM for sucrose and 180 mM mannitol/45 mM sucrose mixture. These concentrations were selected to shift the formulation into the isotonic range. The results of DSC, RALS and ITF testing indicated that trehalose and sucrose had a comparable impact on the thermal stability of MOR208 whereas the mixture of mannitol/sucrose slightly decreased the first transition temperature by approx. 0.8° C.

The impact of polysorbate 20 on the thermal stability of MOR208 was tested using concentrations of 0.02%, 0.04%, 0.08% and 0.12%. The results of the DSC and RALS measurements showed no significant impact of polysorbate 20 at the tested concentrations on the thermal stability of MOR208.

The impact of $MgCl_2$ on the thermal stability of MOR208 was tested using concentrations of 1, 5 and 10 mM. The results of the DSC and RALS measurements showed no significant impact of $MgCl_2$ at the tested concentrations on the thermal stability of MOR208.

Working Example 2: Stability Study of Liquid Formulations for MOR208

Based on the biophysical characterization of MOR208 the following 6 different liquid formulations were tested in a stability study:

The following formulations were selected for the stability study:
Formulation F1: 10 mM Citrate, pH 6.0+0.01% PS 20+150 mM NaCl
Formulation F2: 25 mM Citrate, pH 6.0+0.02% PS 20+125 mM NaCl
Formulation F3: 25 mM Citrate, pH 6.0+0.02% PS 20+200 mM Trehalose
a Formulation F4: 25 mM Citrate, pH 6.0+0.02% PS 20+210 mM Sucrose
a Formulation F5: 25 mM Histidine, pH 6.0+0.02% PS 20+140 mM NaCl
Formulation F6: 25 mM Histidine, pH 6.0+0.02% PS 20+230 mM Trehalose
Formulation F7: 25 mM Succinat, pH 6.0+0.02% PS 20+215 mM Trehalose
Formulation F8: 25 mM Histidine, pH 6.5+0.02% PS 20+240 mM Trehalose The protein concentration was 20 mg/mL for all formulations. From each formulation 10 mL were filled in a 10 mL vial, closed with a coated rubber stopper and stored upside down at a controlled temperature of 25° C. for 12 weeks. Analytical testin g was performed prior storage (t0) after 4, 8 and 12 weeks.

Formulations 1, 3, 5 and 7 generated less subvisible particles over 12 weeks compared to the other formulations. The particles were measured by MFI. Formulation 5 showed the lowest number of SVP in the range >10 µm and >25 µm.

The aggregate and monomer level of the formulations was tested by HP SEC. Formulations 2, 3, 7 and 8 showed a higher increase in aggregates over 12 weeks compared to the other formulations.

The osmolality of formulation 4 increased after 4 weeks of storage which most probably indicates the degradation of sucrose contained in the formulation.

The shift in pH also indicates the degradation of sucrose in formulation 4.

Further HIC testing indicated that formulations 6, 7 and 8 showed a stronger decrease in peak 3 area % compared to the other formulations. Especially formulation 8 showed a strong reduction from 66.1% (initial value) to 52.2% after 12 weeks.

The physicochemical characterization of MOR208 identified the most stable pH range between pH 6.0 and 7.0.

Citrate, Histidine and Succinate buffer were selected as pharmaceutical acceptable buffer systems in the mentioned pH range. All buffer systems were used at a concentration of 25 mM providing sufficient buffer capacity for a protein concentration of 20 mg/mL. The addition of NaCl at a minimum concentration of 125 mM had a weak positive effect on the thermal stability of MOR208 (based on DSC data). The addition of sucrose, trehalose, mannitol/sucrose and polysorbate 20 did not alter the thermal stability of MOR208.

Based on the analytical results the most stable formulations were identified to be F1, F3 and F5.
Formulation F1: 10 mM Citrate, pH 6.0+0.01% PS 20+150 mM NaCl
Formulation F3: 25 mM Citrate, pH 6.0+0.02% PS 20+200 mM Trehalose
a Formulation F5: 25 mM Histidine, pH 6.0+0.02% PS 20+140 mM NaCl Samples of these 3 formulations were further kept at 25° C. for up to 8 months and again tested. Formulations 1 and 5 provided the highest stability but all liquid formulations generated subvisible particles after 8 months above the pharmacopeia specifications (NMT 6000 particles≥10 µm per vial and NMT 600 particles≥25 µm per vial). Therefore the desired shelf life of at least 24 months at 2-8° C. was not be reached by one of the tested liquid formulations with 20 mg/mL protein.

This fact drove the decision to start the development of a lyophilized dosage form.

Working Example 3: Lyophilization Feasibility Study

Formulation 3 and a new Formulation 9 were involved in the lyophilization feasibility study with a concentration of MOR208 at 40 mg/ml:
Formulation 3: 25 mM Citrate
200 mM Trehalose dihydrate
0.02% Polysorbate 20
pH 6.0
Formulation 9: 25 mM Citrate
219 mM Mannitol
29 mM Sucrose
0.02% Polysorbate 20
pH 6.0

Appearance of Lyophilized Drug Product

The appearance of the lyo cake for both formulations was acceptable. The trehalose containing formulation was completely amorphous and shows a higher degree of shrinkage which is just a cosmetic observation and is typically not linked to product quality or stability. The mannitol containing formulation was partially cristalline and provides a cake of high pharmaceutical elegance without shrinkage.

The quality of the lyophilized MOR208 was tested and compared to the product quality prior lyophilization. The following Table 1 summarizes the results of Formulations 3 and 9.

procedure. The aggregation level did not increase during lyophilization and a low number of subvisible particles was counted after reconstitution. As a result both formulations are suitable for lyophilization of MOR208 and the lyo-

TABLE 1

Product quality comparison prior an after lyophilization

| | Formulation 3 | | Formulation 9 | |
|---|---|---|---|---|
| | Before Lyophilitzation | After Lyophilitzation | Before Lyophilitzation | After Lyophilitzation |
| Prior reconstitution | | | | |
| Cake appearance | N/A | Acceptable cake appearance | N/A | Acceptable cake appearance |
| Moisture level | N/A | 0.81-0.84% | N/A | 1.19-1.36% |
| Post reconstitution | | | | |
| Reconstitution time/n = 2 | N/A | 48 sec | N/A | 55 sec |
| Reconstitution behavior | N/A | foam formation | N/A | foam formation |
| Visual inspection | opalescent, colourless, no visible particles | opalescent, colourless, no visible particles | opalescent, colourless, no visible particles | opalescent, colourless, no visible particles |
| Turbidity | 22 FNU | 21 FNU | 23 FNU | 22 FNU |
| Osmolality/mOsm · kg$^{-1}$ | 318 | 283 | 356 | 325 |
| pH | 6.1 | 6.1 | 6.1 | 6.1 |
| UV scan | 41.0 mg/mL | 36.9 mg/mL | 40.8 mg/mL | 38.6 mg/mL |
| HPSEC (aggregate %) | 0.8 | 0.8 | 0.7 | 0.8 |
| HPSEC (monomer %) | 99.2 | 99.2 | 99.3 | 99.2 |
| HPSEC (fragments %) | 0.0 | 0.0 | 0.0 | 0.0 |
| Subvisible particles | n.d. | 76 ≥ 10 μm/mL 9 ≥ 25 μm/mL | n.d. | 71 ≥ 10 μm/mL 12 ≥ 25 μm/mL |
| IEC neutral peaks % | 82.1 | 82.4 | 82.1 | 82.3 |
| IEC post peaks % | 6.6 | 6.3 | 6.5 | 6.3 |
| IEC pre peaks % | 11.4 | 11.3 | 11.4 | 11.4 |
| CD16 binding | 103 | 99 | 105 | 103 |
| HIC pre peaks % | 0.38 | 0.39 | 0.39 | 0.39 |
| HIC peak 1% | 0.98 | 1.19 | 0.97 | 1.22 |
| HIC peak 2% | 4.25 | 3.73 | 4.06 | 3.95 |
| HIC peak 3% | 86.59 | 86.66 | 86.75 | 86.82 |
| HIC post peaks % | 7.79 | 8.02 | 7.83 | 7.62 |

An additional lyophilization study was performed which only focused on subvisible particle (SVP) testing prior and post lyophilization. Results of the study are listed in Table 2 clearly indicating that the lyophilization process did not increase the SVP count.

TABLE 2

Subvisible particle count of MOR208-F3 prior an post lyophilization

| | Sub-visible particles per mL (MFI) | | |
|---|---|---|---|
| Sample | 2-1000 μm | ≥10 μm | ≥25 μm |
| MOR208-F3 before lyophilisation | 847 | 46 | 5 |
| lyo MOR208-F3 after reconstitution | 892 | 15 | 2 |

Based on the test results no negative impact of the lyophilization process on product quality was observed. Both formulations provide an acceptable cake appearance. The reconstitution time is below 60 seconds for the formulation containing 40 mg protein per mL. Reconstitution is performed by adding 5 mL of water for injection. The moisture level of the mannitol/sucrose formulation is higher compared to the trehalose containing formulation which is due to the higher density of the lyo cake. The osmolality and the protein content (UV scan) decreased after lyophilization because the product was diluted due to the reconstitution philization feasibility study was successfully finished. Following this study an accelerated stability study with both formulations was performed over a period of 3 months at 40° C.

Working Example 4: Accelerated Stability Study

After the lyophilization feasibility study was successfully finalized a first stability study at 40° C. (75% rH) over 3 months was executed to compare both formulations. The stability testing included testing for color and visible particles. Furthermore the products were tested for HP-SEC (Aggregation), HIC, IEC, binding assay (CD16 Biacore), MFI (sub-visible particles) and SDS-Page.

HP-SEC testing showed a higher increase in aggregates for F9 after 3 months of storage (Table 3). The aggregate level for F3 increased from 0.8% to 1.7% where the aggregate level of F9 increased from 0.8% to 2.6%.

TABLE 3

Aggregate testing by HP-SEC

| | Formulation 3 | | Formulation 9 | |
|---|---|---|---|---|
| | aggregates/% | monomer content/% | aggregates/% | monomer content/% |
| Initial value | 0.8 | 99.3 | 0.8 | 99.2 |
| 1 month | 1.4 | 98.6 | 2.2 | 97.8 |

TABLE 3-continued

| Aggregate testing by HP-SEC | | | |
|---|---|---|---|
| | Formulation 3 | | Formulation 9 |
| | aggregates/% | monomer content/% | aggregates/% monomer content/% |
| 2 months | 1.8 | 98.2 | 2.1 97.9 |
| 3 months | 1.7 | 98.3 | 2.6 97.4 |

The subvisible particles were tested for t0 and after 4 weeks, 8 weeks and 12 weeks with the MFI method. Comparing both formulations it was obvious that the mannitol/sucrose formulation generated more particles over time especially in the range between 2 μm and 1000 μm (FIG. 2).

Based on the analytical results, formulation 3 containing trehalose showed a higher stability at 40° C. compared to formulation 9. Differences in stability were seen in SVP (MFI) and aggregate level (HPSEC).

Conclusion:

The lyophilization feasibility study showed that MOR208 can be freeze dried without an impact on product quality using both formulations and a protein concentration of 40 mg/mL. The stability conditions were 40° C. (75% rH) over a period of 3 mo nths. During this stability study the trehalose containing formulation was identified with a higher stability compared to the mannitol/sucrose formulation.

Working Example 5: Shelf Life Assignment

For a long term stability study MOR208 in Formulation 3 was put on real time storage at 5° C.±3° C. and accelerated storage at 25° C.±2° C. testing.

The performed stability studies comprise stability indicating and state of the art methods to monitor Drug Products regarding concentration, activity, purity, pharmaceutical and microbiological parameters during storage.

The following parameter methods were used and are considered to be the main stability indicating tests:

Purity by HP-SEC:

Stability indicating properties of HP-SEC were shown by analysis of a relevant stress sample.

Moreover, the capability of aggregate detection was verified by analytical ultracentrifugation.

Homogeneity and Purity by IEC and Reduced/Non-Reduced CGE:

For detection of fragments non-reducing CGE is applied; chemical modifications which lead to charge variants like deamidation were detected by IEC.

Activity Assays:

The product specific activity assays CD19 binding assay (FACS), CD16 binding assay (SPR) and ADCC potency assay showed sensitivity to a relevant stress sample.

Results of the Real Time Storage at 5° C.±3° C. and the Accelerated Storage at 25° C.±3° C. are summarized in Table 4 and Table 5 respectively.

TABLE 4

| MOR208 - Real Time Storage at 5° C. ± 3° C. | | | | | | | |
|---|---|---|---|---|---|---|---|
| Parameter | Specification | 0 months | 6 months | 12 months | 18 months | 24 months | 36 months |
| Visible particles | Solution essentially free of foreign particles, may contain few white to whitish product-typical particles | Essentially free of foreign particles; no translucent, white to whitish particles contained | | | | | |
| IEC [%] | Report result Acidic Peak Group | 24.1 | 24.7 | 24.5 | 24.4 | 24.3 | 24.3 |
| | Report result Main Peak Group | 66.3 | 65.5 | 65.5 | 66.0 | 65.8 | 65.6 |
| | Report result Basic Peak Group | 9.7 | 9.8 | 10.0 | 9.6 | 9.9 | 10.1 |
| HP-SEC[%] | Monomer ≥92 | 98 | 97 | 98 | 98 | 98 | 98 |
| | Aggregates ≤5 | 2 | 3 | 2 | 2 | 2 | 2 |
| CGE reduced [%] | Σ heavy and light chains ≥90 | 97 | 97 | 96 | 97 | 97 | 96 |
| CGE non reduced [%] | Main peak ≥85 | 92 | 93 | 93 | 93 | 93 | 93 |
| | Fragments: Report result | 6 | 6 | 6 | 6 | 6 | 6 |
| Potency assay (ADCC) [%] | 50-150 of standard material | 78 | 118 | 99 | 98 | 99 | 97 |
| CD19 binding assay (FACS) [%] | 50-150 of standard material | 97 | 92 | 96 | 106 | 109 | 83 |
| CD16 binding assay (SPR) [%] | 50-150 of standard material | 96 | 97 | 101 | 100 | 100 | 93 |
| Sub-visible Particles [particles/vial] | ≥10 μm: ≤6000 particles/vial | 10 | 7 | 347 | 93 | 167 | 113 |
| | ≥25 μm: ≤600 particles/vial | 0 | 0 | 3 | 3 | 0 | 10 |
| Sub-visible particles (MFI) [particles/mL] | Report result particles ≥2 to <10 μm | 3499 | 6027 | 21417 | 9265 | 5639 | 9632 |

TABLE 5

| MOR208 - Accelerated Storage at 25° C. ± 3° C. | | | | | |
|---|---|---|---|---|---|
| Parameter | Specification | 0 months | 1 months | 3 months | 6 months |
| Visible particles | Solution essentially free of foreign particles, may contain few white to whitish product-typical particles | Essentially free of foreign particles; no translucent, white to whitish particles contained | | | |

TABLE 5-continued

| MOR208 - Accelerated Storage at 25° C. ± 3° C. | | | | | |
|---|---|---|---|---|---|
| Parameter | Specification | 0 months | 1 months | 3 months | 6 months |
| IEC [%] | Report result Acidic Peak Group | 24.1 | 23.9 | 24.6 | 24.8 |
| | Report result Main Peak Group | 66.3 | 66.0 | 64.7 | 64.1 |
| | Report result Basic Peak Group | 9.7 | 10.1 | 10.7 | 11.2 |
| HP-SEC[%] | Monomer ≥92 | 98 | 98 | 98 | 97 |
| | Aggregates ≤5 | 2 | 2 | 2 | 3 |
| CGE reduced [%] | Σ heavy and light chains ≥90 | 97 | 97 | 97 | 96 |
| CGE non reduced [%] | Main peak ≥85 | 92 | 93 | 93 | 93 |
| | Fragments: Report result | 6 | 6 | 6 | 6 |
| Potency assay (ADCC) [%] | 50-150 of standard material | 78 | 99 | 102 | 97 |
| CD19 binding assay (FACS) [%] | 50-150 of standard material | 97 | 97 | 93 | 101 |
| CD16 binding assay (SPR) [%] | 50-150 of standard material | 96 | 99 | 104 | 91 |
| Sub-visible Particles [particles/vial] | ≥10 μm: ≤6000 particles/vial | 10 | 117 | 433 | 50 |
| | ≥25 μm: ≤600 particles/vial | 0 | 3 | 57 | 0 |
| Sub-visible particles (MFI) [particles/mL] | Report result particles ≥2 to <10 μm | 3499 | 9861 | 9744 | 3777 |

Discussion of Results:

Content and Activity

The functional activity of MOR208 was monitored with three different activity assays: CD19 binding assay (FACS), CD16 binding assay (SPR) and an ADCC based potency assay. With the combination of these three assays the antigen binding, the relevant effector binding as well as the major mode of action (ADCC) are covered.

Both binding assays show no clear or relevant tendencies over time. The ADCC based potency assay shows some increase over time (both under real term and accelerated conditions) but as the assay also shows a higher variability the tendency is not yet considered to be significant. In summary, all content and activity assays are well within the specification and do not indicate any critical changes in product quality over 36 months.

Purity

During 36 months of storage at the intended storage temperature 5±3° C. none of the purity assays (i.e. HP-SEC, IEC, reducing and non-reducing CGE) indicate critical changes in product purity. Under accelerated conditions at 25° C.±2° C. the HP-SEC s hows only one change in the values at the latest testing point (decreased monomer/increased fragment values for one increment) but this is not reflected by long term data and is therefore considered negligible. IEC shows no tendencies under long term conditions but a clear tendency to a decreasing main peak group/increasing basic peak group under accelerated conditions.

In summary, all purity assays are well within the specification and do not indicate critical changes in product quality over 36 months.

Pharmaceutical Tests

During 36 months of storage at the intended storage temperature 5±3° C. none of the pharmaceutical tests indicated a critical change over time. In summary, all pharmaceutical tests are well within the specification and do not indicate critical changes in product quality over 36 months.

We claim:

1. A lyophilized pharmaceutical formulation comprising an anti-CD19 antibody,
   wherein the lyophilized pharmaceutical formulation is stable at 2-8° C. for at least 24 months,
   wherein the formulation prior to lyophilization comprises a buffer with a pH range of about 5.6 to about 7.0 in a concentration of between 10 and 75 mM,
   polysorbate in a concentration of 0.005% (w/v) to 0.06% (w/v), and
   (a) trehalose in a concentration of 180 mM to 240 mM or
   (b) mannitol in a concentration of 180 mM to 240 mM and sucrose in a concentration of 10 mM to 50 mM; and
   the anti-CD19 antibody in a concentration of 20 mg/ml to 125 mg/ml,
   wherein the anti-CD19 antibody comprises a HCDR1 region of sequence SYVMH (SEQ ID NO:1), an HCDR2 region of sequence NPYNDG (SEQ ID NO:2), an HCDR3 region of sequence GTYYYGTRVFDY (SEQ ID NO:3), an LCDR1 region of sequence RSSKSLQNVNGNTYLY (SEQ ID NO:4), an LCDR2 region of sequence RMSNLNS (SEQ ID NO:5), and an LCDR3 region of sequence MQHLEYPIT (SEQ ID NO:6), and
   wherein the anti-CD19 antibody comprises a heavy chain constant domain of the sequence ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPDVFLFPPKPKDTLMISRTPEVTCVVVDVSHEDPEVQFNWYVDGVEVHNAKTKPREEQFNSTFRVVSVLTVV HQDWLNGKEYKCKVSNKALPAPEEKTISKTKGQPREPQVYTLPPSREEMTKNQVSLTCLVKGFY PSDIAVEWESNGQPENNYKTTPPMLDSDGSFFLYSKLTVDKSRWQQGNVFSCSVMHEALHNHYTQKSLSLSPGK (SEQ ID NO:8) and a light chain constant domain of the sequence RTVAAPSVFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC (SEQ ID NO:9).

2. The formulation of claim 1, wherein the formulation prior to lyophilization comprises the anti-CD19 antibody in a concentration of 40 mg/ml.

3. The formulation of claim 1, wherein the buffer is a citrate buffer or a phosphate buffer.

4. The formulation of claim 3, wherein the formulation prior to lyophilization comprises the citrate buffer or the phosphate buffer in a concentration of between 20 and 50 mM.

5. The formulation of claim 3, wherein the formulation prior to lyophilization comprises the citrate buffer or the phosphate buffer in a concentration of 25 mM.

6. The formulation of claim 1, wherein the formulation prior to lyophilization comprises trehalose in a concentration of 200 mM.

7. The formulation of claim 1, wherein the formulation prior to lyophilization comprises mannitol in a concentration of 219 mM and sucrose in a concentration of 29 mM.

8. The formulation of claim 1, wherein the polysorbate is polysorbate 20.

9. The formulation of claim 1, wherein the formulation prior to lyophilization comprises polysorbate in a concentration of 0.02% (w/v).

10. The formulation of claim 1, wherein the anti-CD19 antibody comprises a variable heavy chain of the sequence EVQLVESGGGLVKPGGSLKLSCAASGYTFTSYVMHWVRQAPGKGLEWIGYINPYNDGTKYNEKFQGRVTISSDKSISTAYMELSSLRSEDTAMYYCARGTYYYGTRVFDYWGQGTLVTVSS (SEQ ID NO:10) and a variable light chain of the sequence DIVMTQSPATLSLSPGERATLSCRSSKSLQNVNGNTYLYWFQQKPGQSPQLLIYRMSNLNSGVPDRFSGSGSGTEFTLTISSLEPEDFAVYYCMQHLEYPITFGAGTKLEIK (SEQ ID NO:11).

11. The formulation of claim 1, wherein the formulation prior to lyophilization comprises the anti-CD19 antibody in a concentration of 40 mg/mL, a citrate buffer in a concentration of 25 mM, trehalose in a concentration of 200 mM, polysorbate in a concentration of 0.02% (w/v), and has a pH of 6.0.

12. The formulation of claim 1, wherein the formulation prior to lyophilization comprises the anti-CD19 antibody in a concentration of 40 mg/mL, a citrate buffer in a concentration of 25 mM, mannitol in a concentration of 219 mM, sucrose in a concentration of 29 mM, polysorbate in a concentration of 0.02% (w/v), and has a pH of 6.0.

* * * * *